United States Patent [19]

Schram

[11] Patent Number: 5,006,266
[45] Date of Patent: Apr. 9, 1991

[54] MANIPULATING MEANS UTILIZING ULTRASONIC WAVE ENERGY FOR USE WITH PARTICULATE MATERIAL

[75] Inventor: Cornelius J. Schram, Pavenham, England

[73] Assignee: National Research Development Corporation, London, England

[21] Appl. No.: 375,010

[22] PCT Filed: Oct. 13, 1988

[86] PCT No.: PCT/GB88/00849
§ 371 Date: Aug. 2, 1989
§ 102(e) Date: Aug. 2, 1989

[87] PCT Pub. No.: WO89/03243
PCT Pub. Date: Apr. 20, 1989

[30] Foreign Application Priority Data

Oct. 14, 1987 [GB] United Kingdom ............... 8724067

[51] Int. Cl.$^5$ .............................................. B01D 43/00
[52] U.S. Cl. ............................. 210/748; 210/542; 209/1; 209/155; 73/505
[58] Field of Search ................ 210/748, 542; 209/1, 209/155–159, 461; 73/505

[56] References Cited

U.S. PATENT DOCUMENTS 4,759,775  7/1988  Peterson et al. ............... 210/748
4,877,516 10/1989  Schram ............................ 209/155

FOREIGN PATENT DOCUMENTS 0147032  3/1985  European Pat. Off. .
2098498 11/1982  United Kingdom .............. 210/748
2173420 10/1986  United Kingdom .

OTHER PUBLICATIONS

IBM Technical Disclosure Bulletin, vol. 25, No. 1, Jun. 1982 (New York, US), H. W. Curtis et al., pp. 192–193, see the whole document.
WO, A, 85/01892 (UNILEVER), 9 May 1985 see abstract, p. 3, line 23, p. 4, line 26, claims 1, 2, 10.
WO, A, 87/07178 (UNILEVER), 3 Dec. 1987 see abstract, p. 12, line 2, p. 16, line 12, Figures 3–8.

Primary Examiner—W. Gary Jones
Assistant Examiner—Matthew O. Savage
Attorney, Agent, or Firm—Cushman, Darby & Cushman

[57] ABSTRACT

Particulate material influenced by the acoustic forces in an ultrasonic standing wave is manipulated in a liquid column (16) by the use of at least two standing waves having axes extending transversely across the column at different orientations to its longitudinal axis. The nodes of the standing waves intersect within the column to give regions of greatest acoustic influence that allows a relative displacement between the particles and the liquid in a direction transverse to the axes of the standing waves. The effects of acoustic streaming can be reduced and the physical arrangement of the ultrasound apparatus in relation to the column is simplified.

19 Claims, 3 Drawing Sheets

MANIPULATING MEANS UTILIZING ULTRASONIC WAVE ENERGY FOR USE WITH PARTICULATE MATERIAL

This invention relates to the use of ultrasonic wave energy for the manipulation of particulate material in a liquid medium.

The particulate material is influenced by the acoustic forces in an ultrasonic standing wave which attracts the individual particles to the nodes or the antinodes (for the purposes of the present invention it is immaterial which and to simplify the following description only the nodes will be referred to and it is to be understood that the mechanisms are identical for such particles as are attracted by the antinodes)

In our European patent application 147032 (84.307496.4) there is described how two axially opposed ultrasonic transducers can establish a standing wave to control the movement of particles in a coaxial column of liquid interposed between the transducers, and how, by displacing the standing wave, it is possible to move particles under the influence of the standing wave along the column in the axial direction of the standing wave.

The working length of the standing wave occupies only a part of the axial spacing between the transducers because although the transducers may be matched to give corresponding power outputs, attenuation of the ultrasonic energy as it travels along the column causes an increasing imbalance between the two outputs at different points along the column as the distance from the midpoint between the two transducers increases Attenuation is experienced as an acoustic energy gradient in the direction of propagation of the standing wave and these gradients generate unwanted acoustic streaming in the liquid along the column in a direction parallel to that in which the particles are being displaced Because the rate of attenuation increases with the frequency of the transducer output, this effect is more pronounced at higher ultrasonic frequencies and the effective working length of the standing wave can be reduced to only a very small part of the distance between the transducers The use of high frequency ultrasonic sources, e.g. 100 kHz upwards, also means that air must be totally excluded from the system because ultrasound is rapidly attenuated in air at such frequencies making it effectively a non-conductor There must be no air gaps, therefore, between the transducers and the column, nor can bubbles be allowed to exist in the liquid.

Obviously, problems arise if these conditions cannot conveniently be fulfilled. As an example, if it is required to employ a high frequency ultrasonic system for separation and/or analysis of particulate material in a column of liquid, so as to subject the column to a standing wave along the whole length, a method of operation may be required that allows this to be done even when the liquid column terminates at a liquid-gas interface.

According to one aspect of the present invention, there is provided apparatus for controlling the movement of particulate material in a liquid column comprising ultrasonic generating means for producing at least two standing waves that have axes extending transversely across the column at different orientations to the longitudinal axis of the column, the standing waves intersecting within the column, and means being provided for relative movement along the column between the intersections of the nodes of the standing waves and the particle-containing liquid in the column.

The invention also provides a method of controlling the movement of particulate material in a liquid column wherein at least two ultrasonic standing waves are established with axes extending transversely across the column at different orientations to the longitudinal axis of the column and intersecting within the column to retain particulate material at the intersections of the standing waves, and by relative movement along the column between the column and said intersections, the material retained at said intersections is displaced in the liquid medium.

Because of the different orientations of the standing waves produced by the ultrasonic generating means in an arrangement according to the invention, the standing waves interact to form an array of intersecting nodes. A significant feature of such an arrangement is that the regions of greatest influence on the particles responsive to the acoustic energy can then be established in relation to the intersections of the nodes of the intersecting standing waves. If one or more of the intersecting standing waves is displaced so as to produce a movement of the intersections relative to the liquid, the particles influenced by the standing waves will move similarly. Consequently a controlled displacement of the particles relative to the liquid can be imposed in a direction transverse to the axes of the standing waves.

A major consequence of this mechanism is that acoustic streaming need no longer act in the same direction as the direction of movement of the particles and it can be arranged that any acoustic streaming has at most a minor component along the column. In addition, it is not necessary to set up ultrasonic transducers coaxially with the column to move particles along the column. Coupling the acoustic energy to the column can be simplified by the fact that paths for the energy do not have to extend through the full length of the column; each standing wave need only have a relatively short path through the liquid carrying the particles.

In the performance of the invention, depending upon the particular embodiment employed, the displacement of the nodes relative to the liquid column can be achieved either by displacing the liquid column axially or by moving the array of intersecting nodal fronts through the common zone of action of the standing waves. It is also possible to displace both the column and the intersecting nodal fronts simultaneously.

In one form of the invention the generating means are arranged to produce standing waves that extend across the column at opposite and equal inclinations relative to the column axis. In this way the nodal intersections can be made to travel axially in the column using generating means that operate at essentially the same frequency. One simple arrangement comprises four ultrasonic transducers set in a diamond pattern but spaced apart both axially and radially In each diagonally opposite pair the outputs from the transducers are matched and follow substantially coaxial paths so that each pair produces a standing wave, and the outputs from all the transducers are coplanar, resulting in an array of intersecting nodal "surfaces" or fronts. It is also possible to dispose the transducers so the outputs from different pairs of transducers have their axes in different radial planes relative to the column, so that a three-dimensional interference pattern results.

In another form of the invention one standing wave with its axis extending obliquely across the column intersects in the column with another standing wave having its axis perpendicular to the column. With the second standing wave stationary, movement of the first standing wave causes the nodal intersections to travel along the column. In such an arrangement the stationary standing wave can be highly resonant and attract particles strongly to its nodal planes. The moving standing wave needs only to be sufficiently strong to ensure that particles held by the stationary wave can be moved through the relatively weak energy gradients that will exist in the nodal planes.

In a preferred form of construction in accordance with the invention, at least when the ultrasonic generating means have emitting faces arranged to transmit ultrasonic energy obliquely to the column, they do so through a medium in which sound travels at an appreciably higher velocity than in the liquid in the column. With such an arrangement, the refraction of the standing waves meeting the interface between the transmitting medium and the liquid obliquely to that interface, deflects the axis of propagation in the liquid closer to a normal to the column axis. It is thereby possible to arrange that a greater part of the zones of action of the respective standing waves intersect within the column while the more acute inclination of the or each obliquely oriented standing wave axis in the transmitting medium rapidly increases the spacing between respective standing waves outside the column and so makes it easier to accommodate transducers of the ultrasonic generating means at convenient positions in relation to the column.

The invention will be described by way of example by reference to the accompanying schematic drawings, in which.

Figure 1:
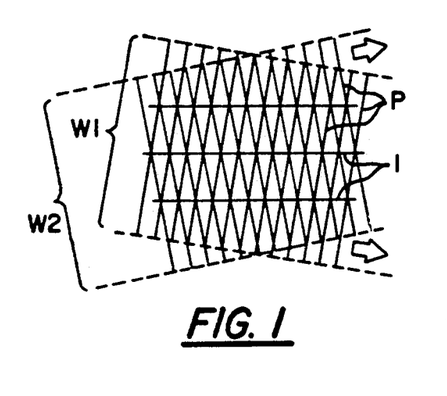
FIG. 1 is an explanatory diagram illustrating an interference pattern formed by the interaction of two intersecting beams of ultrasonic energy.

FIG. 1 illustrates the intersection of two progressive waves W1, W2, both travelling to the right in the figure, along axes at a small angular divergence from each other, the waves having the same frequency. Wave fronts, indicated as a series of planar fronts P for each wave, travel along the axes of their respective waves at the sonic velocity in the medium. The wave fronts of the two waves form a series of points of intersection that travel with the fronts along paths I parallel to the bisector of the axes of the two waves and form nodal fronts of a standing wave. The smaller the angle between the directions of propagation of the progressive wave becomes, the weaker is the standing wave.

Figure 2:
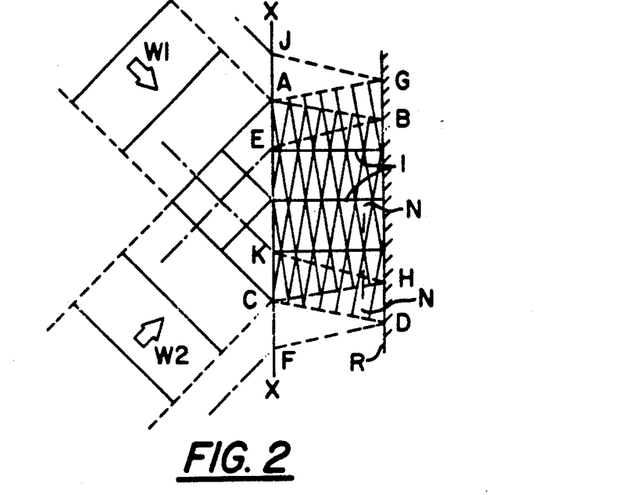
FIGS. 2 and 3 are representations of arrays of intersecting nodal fronts in ultrasonic systems incorporating the invention.

If a reflecting face R normal to the bisectors is placed in front of the wave patterns shown in FIG. 1, normal to the paths I, a regime such as that shown in FIG. 2 may be obtained. FIG. 2 shows the intersection of the two waves in one medium, between the reflecting face R and a boundary X—X which represents the interface with a second medium in which the sonic velocity is greater, e.g. the first medium being a liquid such as water and the second medium being a solid sound-transmitting medium such as aluminium. The use of the second medium allows the ultrasonic sources (not shown) to be more conveniently spaced apart while maintaining the axes of the waves in the second medium at only a small angle to the normal from the reflecting face. The incident path of one wave W1 through the first medium is bounded by the lines AB and CD and its reflected path by the lines BE and DF. The other wave has its incident path bounded by the lines AG and CH and its reflected path by the lines GJ and HK. All four paths share the volume EBHK within which a series of standing waves are set up. Firstly, by matching the frequencies of the two waves W1, W2, two standing waves are set up each formed by the incident beam of one progressive wave and the reflected beam of the other. These two standing waves cross each other obliquely and each has its nodal fronts oblique to the reflector R.

In the space between the boundary X—X and the reflector R, each of the progressive waves W1, W2 also forms a standing wave with its own reflection from the reflector R and each of these standing waves has nodal fronts parallel with the reflector R. These standing waves are stationary and fixed in position since they are each generated by reflection. If the progressive waves W1, W2 have the same frequency and travel along axes equally and oppositely inclined to the reflector, their standing waves are indistinguishable from each other and each contributes equally to a resultant single standing wave with nodal fronts parallel to the reflector.

Finally, a further standing wave is formed with nodal fronts parallel to the bisector of the two waves W1, W2, by the interaction of the two waves as they travel towards the reflector R, in the manner already described with reference to FIG. 1. The reflected waves returning from the reflector R interact correspondingly to reinforce this last standing wave.

Both the first pair of standing waves crossing obliquely and the last-mentioned standing wave with fronts parallel to the bisector of the two progressive waves may have their nodal fronts displaced by a sequence of phase changes between the two sources (e.g. in the manner disclosed in our earlier European patent application No. 85.304807 (EP-A-0173435)) since these three standing waves are each formed in the interference between two progressive waves from different sources.

The wave system resulting from the arrangement shown in FIG. 2 is therefore one in which four standing waves exist, the nodal fronts of two of them crossing obliquely and the nodal fronts of the other two lying parallel to and transverse to the reflector, but only the nodes parallel to the reflector cannot be given a progressive movement.

Particles suspended in the liquid and influenced by the acoustic energy will tend to aggregate around all the nodal fronts, but will move in particular to the regions where these fronts intersect. By displacing the mobile standing wave up or down in the liquid between the boundary X—X and the reflector R, the particles are correspondingly displaced relative to the liquid.

The rigid medium coupling the ultrasound source acoustically to the liquid is so chosen as to minimize attenuation of the ultrasonic energy in its passage through the medium, but attenuation effects are nevertheless accentuated by the use of the reflecting face to establish the standing waves since some energy loss will be experienced at that face. Because of the very small inclination of the axes of energy propagation relative to the nodes of the standing waves extending normal to the reflector, such acoustic streaming as is generated has a proportionately small influence on the attachment of particles to those nodes and on that account can possibly be tolerated.

Figure 3:
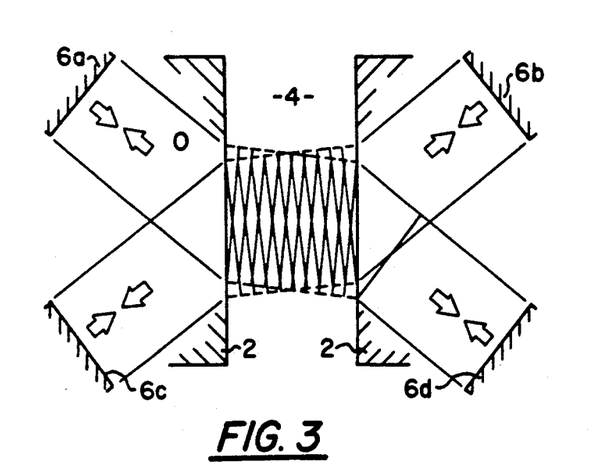

FIG. 3 illustrates an arrangement in which two pairs of opposed transducers each produce a standing wave to form a nodal pattern in a columnar working space by interaction with each other. It shows two wall blocks 2 which define between them a parallel-sided space 4 filled with liquid The transducers, in the form of flat, rectangular emitter plates 6a, 6b, 6c, 6d, e.g. of lead zirconate titanate ceramic composition, are disposed on opposite sides of the space in a symmetrical diamond-form array in which the axis of propagation of the energy from each transducer meets the parallel sides of the liquid-filled space at an angle of incidence "$\theta$". The wall blocks and the liquid in the space are transmitters of ultrasound, but the sonic velocity in the material of the walls is greater than that in the liquid so that, as in the preceding example, there is refraction of the emission at the solid/liquid interface.

The transducers 6a, 6d and 6b, 6c respectively, are aligned in diagonally opposed pairs, so that the two beams of the transducers 6a, 6d have a common path, as have the beams of the pair of transducers 6b, 6c. All the transducers have matched frequencies and output intensities The diagonally opposed pairs of transducers 6a, 6d and 6b, 6c thus each generate a standing wave which extends through the wall blocks and the liquid-filled working space. Since each of these standing waves is generated from two different sources, they can be displaced along the working space by sequential phase changes, as already described. The axes of the beams intersect substantially in the central axial plane of the liquid-filled space.

Similarly to the example of FIG. 2, the nodal system generated by the arrangement of FIG. 3 comprises two nodal arrays with the nodal fronts of each set at a small angle to the bounding planes of the liquid-filled space and the nodal fronts of the two arrays crossing each other at a small angle. Each pair of diagonally opposed transducers (6a, 6d or 6b, 6c) produces its own nodal array by interaction of the incident energy from the transducers and the nodal fronts of the two arrays crossing each other at a small angle. The incident energy from each two diametrically opposed transducers (6a, 6b or 6c, 6d) also interacts to produce a nodal array parallel to the sides of the liquid-filled space and, similarly from each pair of axially opposed transducers (6a, 6c or 6b, 6d), the incident energy produces a nodal array normal to the side walls, this last array being relatively weak because of the small angle between the beams.

As will be described below, it may be an advantage to match the ultrasonic frequency employed to the distance of propagation across the liquid space. In this way the nodal arrays described can be reinforced by reflected energy, each reflection at solid liquid interface behaving in the same manner as the incident beam with the same axis of propagation, i.e. it interacts with all the intersecting incident and reflected beams having each of the three other directions of propagation.

Figure 3A:
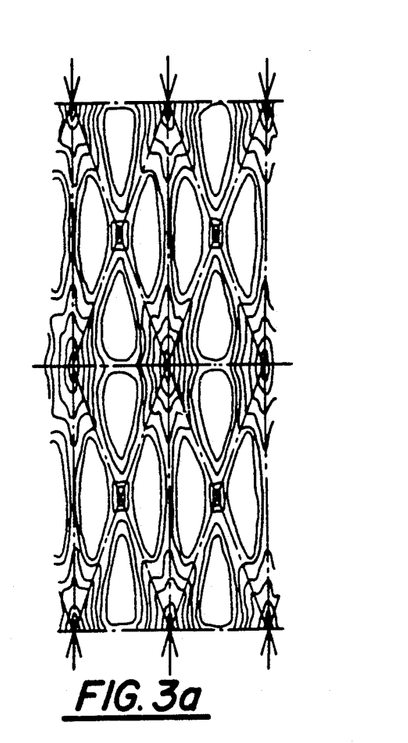
FIG. 3a illustrates the force field in the acoustic system of FIG. 3.

The resultant effect of the superimposed nodal arrays is illustrated schematically in FIG. 3a. The planes of the axial and normal nodal arrays can be represented as a series of rectangular cells with their longer dimension extending axially and the oblique nodal arrays form diagonals of these cells. For a particle in the potential field represented in FIG. 3a, the acoustic forces on the particle are greatest at the corners of each cell where all the nodal arrays intersect. The axial nodal array exhibits stronger forces on the particle than the array normal to the axis but it is characteristic that these forces act on the particle in both the axial and normal directions. As the angle of incidence of the ultrasonic beams diverges further from a normal to the bounding planes of the liquid space, the cell aspect ratio decreases, and the strength of the axial nodal array decreases while that of the array normal to the sides of the liquid space strengthens. This is to be preferred but the increasing internal reflections of the ultrasound as the angle of the beams to the normal increases imposes a limitation.

Particles influenced by the acoustic energy will largely tend to become attached to the axial nodal arrays, although some particles may also be retained by the intersections of the two oblique nodal arrays. If the liquid is moving axially through the space the particles in it will become trapped in the standing wave pattern, provided that the acoustic forces on them exceed the fluid drag forces, so that there is relative displacement between the liquid and the particles. Such displacements can similarly be produced if the transducers of each diagonally opposed pair have their output phases so varied or their output frequencies so adjusted as to give the standing wave they generate a progressive movement through the liquid space. The rates of movement of the two standing waves in FIG. 3 are kept identical and are so arranged that, e.g. the standing wave between the transducers 6a, 6d moves from left to right and that between the transducers 6b, 6c moves from right to left. The intersections of the nodes of the two oblique standing waves therefore move axially, downwards parallel to the sides of the space 4.

Figures 4, 5:
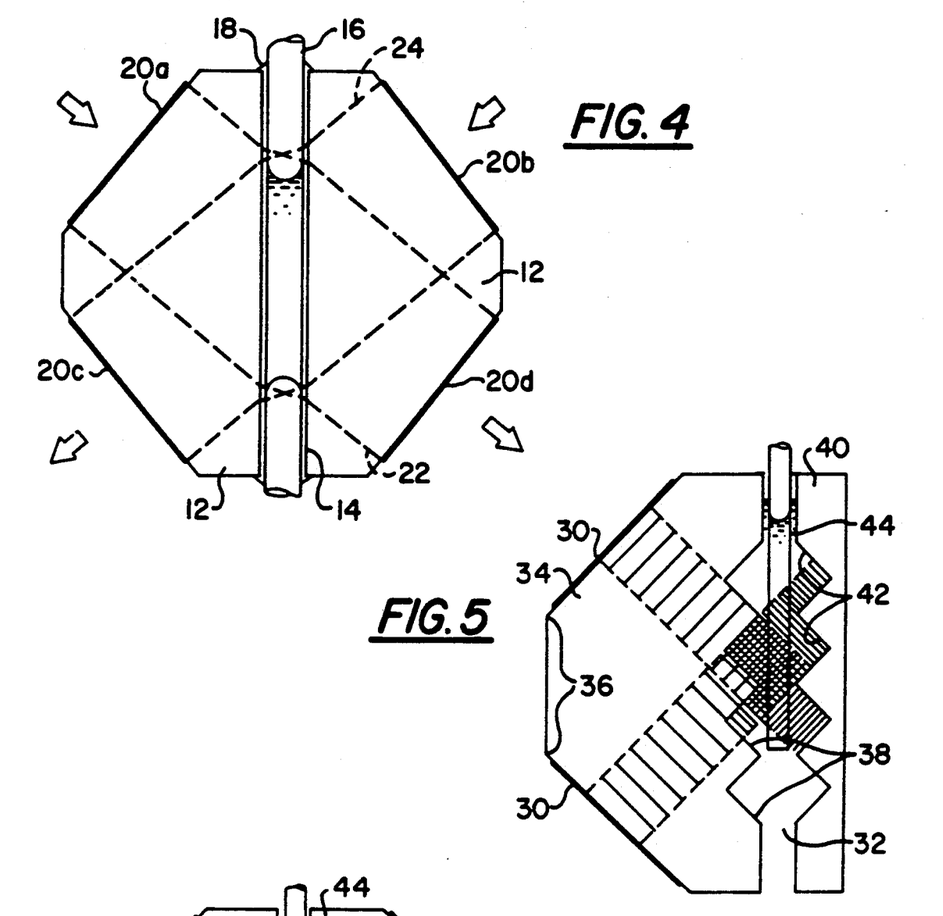
FIG. 4 illustrates the use of the system of FIG. 3 for the separation of particles in a blood sample capillary tube.
FIGS. 5 and 6 illustrates further examples of apparatus according to the invention.

In FIG. 4, the system described with reference to FIG. 3 is shown applied to an apparatus for the concentration of particles in a blood sample capillary tube. Coupling blocks 12 of aluminium define a narrow parallel-sided space 14 through which a capillary tube 16 of an acoustically transparent substance such as polystyrene is a close sliding fit. A thin aqueous film 18 couples the tube to the blocks. The two blocks are symmetrical with respect to a central axial plane of the space between them and a plane normal thereto and have oblique faces to which two pairs of ultrasonic transducers 20a, 20b, 20c, 20d are closely coupled. The arrangement of the transducers corresponds to that described with reference to FIG. 3.

Illustrated in broken lines in FIG. 4 are the beam paths 22,24 of the ultrasonic emissions between the transducers, whereby a standing wave interference pattern is produced in the sample in the capillary tube. Refraction at the solid liquid interface is determined by the formula:

$$\frac{\sin \theta_S}{v_S} = \frac{\sin \theta_L}{v_L}$$

in which $v_S$ and $v_L$ are the sonic velocities in the solid and the liquid respectively, $\theta_S$ is the angle of incidence, and $\theta_L$ is the angle of refraction With the example of aluminium as the coupling block material and an aqueous liquid medium, the sonic velocity in these materials is 6400 m/s and 1500 m/s respectively; if the transducers are set at an angle of 45° to the walls of the space, the transmission through the aqueous medium is thus directed at 80.5° to the walls. Accordingly, over the width of the space, the common zone of action occupied by the interference pattern occupies by far the greatest part of the total volume through which the ultrasonic energy passes. As has already been described, by giving the standing waves a progressive displacement and/or by moving the tube axially between the blocks, particles influenced by the acoustic energy can be collected at one end of the liquid-filled space in the tube.

A further example of an apparatus according to the invention in FIG. 5 shows an arrangement analogous to that in FIG. 2 in that it employs two transducers 30 to one side of a liquid-filled columnar working space 32, each transducer producing a standing wave by reflection from a surface on the opposite side of the space. The transducers are mounted on a coupling block 34, e.g. of aluminium, on faces 36 of that block that are at an angle to each other, conveniently at an angle of 90°. The exit face of the coupling block has an indented form providing exit facets 38 for the respective beams perpendicular to their axes. The reflector 40, which may be a tungsten plate, has a similar indented configuration with reflecting facets 42. The facets 38,42 of each of the opposed surfaces are perpendicular to the axis of the incident beam passing through them or falling upon them. The reflected beam is thus returned from each facet 42 of the plate coaxially with the incident beam upon it to form a standing wave with nodes lying perpendicular to the common axis. For this effect to be achieved, each facet of the coupling block is spaced at an integral number of half wavelengths from its associated transducer and the distance between opposed, parallel facets across the liquid space is also equal to an integral number of half wavelengths.

For clarity, the figure indicates the standing waves over only a part of the width of the transducers, but it will be understood that the width of each standing wave will be substantially the same as that of the transducer generating the beam. In the liquid-filled space 32, therefore, there is a region extending a substantial part of its length containing a system of standing waves on crossing axes similar to the preceding examples, and an acoustically transparent container 44 can be moved along the space, through the crossed wave system, to collect together particles suspended in the liquid in the tube.

Because the acoustic beams pass through or are reflected from solid-liquid boundaries normal to the axis of propagation, no shear waves are generated at these boundaries. By adopting the spacing indicated, a strongly resonant system can be established, showing a high energy density in the liquid. By arranging the axes of propagation at right-angles to each other, the geometry is simplified and it is ensured that the radiation from either transducer is transmitted through or reflected by facets parallel to that transducer It is, however, possible to arrange the axes of propagation at different angles.

It is possible to operate the system described in FIG. 5 in such a way that only the two nodal arrays, with nodes perpendicular to each axis of propagation, are formed. If this is required, however, the frequency of the two transducers should be different If the transducers have a common frequency the two standing waves interact and form a further nodal array in which the nodes lie parallel to the bisector of the angle between the respective axes of propagation. The difference in frequency to avoid this effect need only be small, e.g. 0.1%. (Similar considerations apply, of course, to the arrangement shown in FIG. 3).

Figure 6:
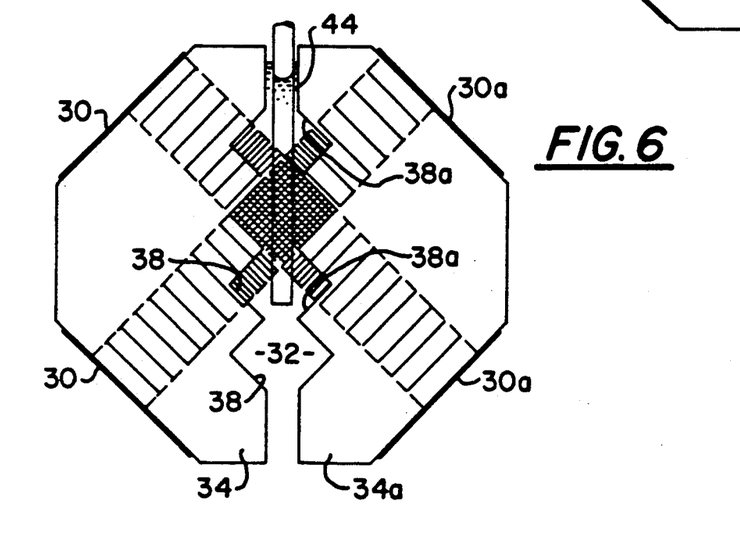

In FIG. 5 each of the standing waves is stationary in the liquid-filled space because it is formed by reflection. Although the additional nodal array just described would result on the interaction of two ultrasonic sources, neither could it generate a controlled movement of this array because of the resonant conditions in the channel. If relative movement is to be obtained in the space between a sample carrier and the standing wave pattern without moving the carrier, it is required to establish a primary standing wave by the interaction of the outputs of two sources of controllable frequencies. This has already been described with reference to FIG. 4, and FIG. 6 illustrates a modification of that arrangement that employs some of the features of FIG. 5. Parts already described with reference to FIG. 5 are indicated by the same reference numbers, and their mirror-image counterparts are identified by the suffix "a". In addition to the coupling block 34 of the previous figure, there is a second, identical coupling block 34a arranged in mirror-image with respect to the central longitudinal axis of the columnar space and at right-angles to the first. As before, for resonance in the liquid-filled space 32 the distances from the transducers 30,30a to their emitting facets 38,38a equals an integral number of half wavelengths, and similarly there is an integral number of half wavelengths between opposed facets of the coupling blocks on opposite sides of the channel. The standing wave pattern in the space 32 is essentially the same as that which appears in FIG. 5, but because each standing wave is generated by two sources 30,30a, the nodal array of each standing wave may be moved by control of the transducer output frequencies, preferably by a method as described in EP-A-0173435 which does not require changes of frequency. If it is required to obtain this movement by control of the transducers, however, it will generally be desirable to limit the degree of resonance in the channel; if resonance is extremely strong there may be a tendency for the nodal arrays to become locked in position because the multiple reflections of the beams will act against any attempt to displace the nodal array of the primary beam.

Figure 7:
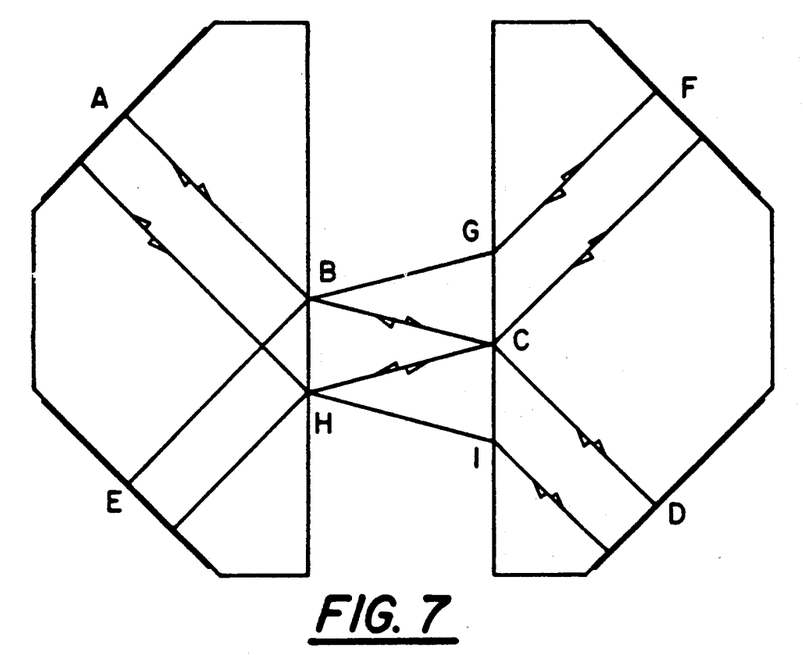
FIG. 7 illustrates how the phenomenon of resonance can be employed in the performance of the invention.

The development of resonant systems can be considered by reference to FIG. 7 which shows a configuration essentially the same as that in FIG. 4 with four transducers arranged in diagonally opposite pairs on opposed coupling blocks with a liquid-filled space between them. If the output from only one transducer is considered at A and account is taken of the fact that the beam incident upon the diagonally opposite transducer will be reflected back from D, a primary standing wave can be formed on the axis BC in the liquid space. The incident beam from A is, however, partially reflected at B on the outlet face of its coupling block and this reflected energy is returned from E by the other transducer of the block acting passively. The reflected energy is partially transmitted through B and G to F, and between E and F, from the second pair of diagonally opposed transducers a corresponding but oppositely inclined standing wave system is therefore set up on the axis BG in the liquid space. Similarly, reflection in the second block of the beam travelling from D to C will set up a further standing wave on the axis CH in the liquid and a still further standing wave, from the axis HI in the liquid, is set up by internal reflections at H. The effect thus spreads to each side of the original axis BC by additional internal reflections in the block provided the degree of resonance and the reflectivity in the block are sufficiently great so that the decay of the secondary and higher order systems does not render them ineffective virtually immediately.

A significant point about the resonant reflecting system just described is that any one of the four transducers can produce a system of crossing standing waves in the liquid channel and the others can be replaced by passive reflectors, although of course the resulting nodal system cannot be given a displacement along the liquid-filled space between the blocks In fact, as a fully resonant system, the arrangement shown in FIG. 7, even with multiple energy sources, cannot provide a displaceable nodal system and it would be necessary to limit the degree of resonance to obtain such a system.

For simplicity of explanation the drawings show arrangement in a given plane. It will be understood, however, that the manner of operation applies equally well to a three-dimensional configuration in which further pairs of transducers are arranged around the central axis of the space between the blocks with their beam axes in a further axially extending plane or planes. Thus, in the example of FIGS. 4 and 6, there may be a further two pairs of transducers producing standing waves on axes in a radial plane at right-angles to the axes of the illustrated standing waves, so that four transducers are spaced around the lower part of the axial liquid space and four around the upper part. Further pairs of transducers can of course be added if required. Similarly, two transducers having frustoconical emitting surfaces can be provided, having a diametrical cross-section conforming to FIG. 4.

Figure 8:
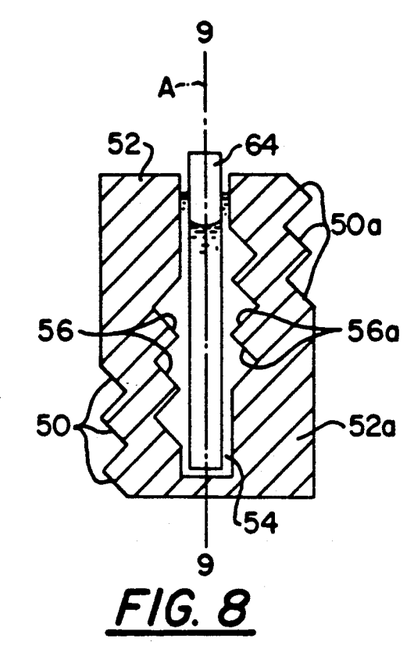
FIGS. 8 and 9 illustrate another example of apparatus according to the invention, being sectional views on the lines VIII—VIII and IX—IX in the figures.
Figure 9:
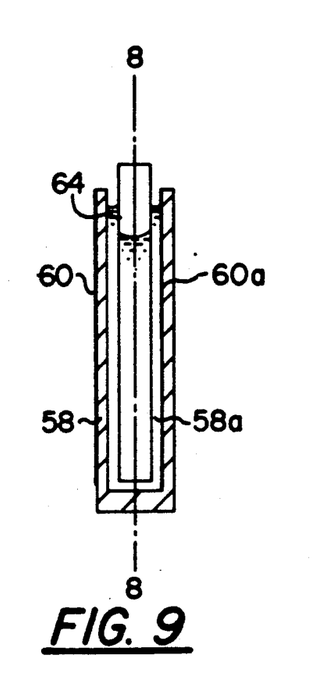

FIGS. 8 and 9 illustrate another example of an apparatus according to the invention with a three-dimensional configuration of the nodal array. Transducers 50,50a are mounted on coupling blocks 52,52a on opposite sides of a liquid-filled space 54 to form opposed, coaxial pairs arranged diagonally to a main longitudinal axis A of the space between them. The blocks bound these two sides of the space, analogously to the example of FIG. 6, have a series of parallel entry and exit faces 56,56a perpendicular to the axes of propagation of the ultrasonic energy from the transducers. The nodal system set up by the transducers on diagonal axes in the space is preferably non-resonant. Bounding the transverse opposite sides of the liquid-filled space 54 are planar containing walls 58,58a, extending parallel to the longitudinal axis of the space and to the axes of the diagonal standing wave system. On the walls 58 is a transducer 60 and a reflector 60a which operate to give a strongly resonant standing wave.

The standing wave system of the pair of transducers 60,60a is able to generate high acoustic forces, because of its resonance, and so bind particles closely to its nodes. Parallel to the nodal plane, however, the acoustic force gradients are relatively small so that particles can be displaced along the space by moving the weaker, non-resonant standing wave system of the first group of transistors 50,50a. Because the standing wave systems are operating in different planes, the nodal intersections of the combined systems are inclined to the longitudinal axis A, but if the material acted upon is enclosed in a vessel 64 of relatively small cross-section, as is shown in FIGS. 8 and 9, that need not have any material effect on the results of the process.

Because the transistors (50,50a and 60,60a) for the two nodal systems are grouped around the operating space in different planes, it may be noted that the effective operating space can be extended indefinitely in the longitudinal direction without the elements of the two systems encroaching on each other's space.

Reference has already been made to advantages that the illustrated arrangements have as compared with a columnar arrangement with transducers coaxial to and at opposite ends of the column. These can now be summarized in the following; higher powers and frequencies may be used, since acoustic streaming that may result from residual imbalance between the two opposed transmissions forming a standing wave is directed largely radially, i.e. transversely to the direction of controlled motion, and because the coupling blocks act as heat sinks for the transducers it is possible to avoid the problem that the air spaces at the ends of the column would pose to the use of a coaxial arrangement for capillary tubes: the coupling block material may also shorten the distance over which near field effects predominate, so that the substantially planar nodal patterns associated with the far field can be obtained in a more compact configuration: finally, a practical advantage is that the transducers do not obstruct access to the working space from either axial direction, while axial alignment of the sample tube is not a problem.

I claim:

1. Apparatus for controlling the movement of particulate material in a liquid column having a longitudinal axis, said apparatus comprising:

generating means for producing at least two ultrasonic waves, each standing wave having a series of nodes with at least some of the nodes of the respective standing waves intersecting in the column, said standing waves having axes of propagation extending transversely across the column at different orientations relative to the column's longitudinal axis, at least one of the standing waves having intersections that are angled relative to said longitudinal axis; and means for relative movement in the direction of said longitudinal axis between said intersections of the nodes and the particle-containing liquid in the column in order to cause relative displacement between said liquid and particles attracted to the nodes.

2. Apparatus according to claim 1 comprising means for producing each standing wave wholly or mainly by reflection from a respective single source.

3. Apparatus according to claim 1 comprising means for producing two standing waves with axes of propagation that lie in mutually angled plates that extend axially of the column.

4. Apparatus according to claim 1 wherein coupling means are disposed between the generating means for at least one of the standing waves and the column, and said coupling means have emitting faces lying oblique to the axis of propagation of said standing wave therethrough, said coupling means being of a medium in which the sonic velocity is substantially higher than in the liquid of the column.

5. Apparatus according to claim 1 wherein coupling means are disposed between the generating means for at least one of the standing waves and the column, and said coupling means have emitting faces perpendicular to the axis of propagation of said standing wave but oblique to the longitudinal axis of the column.

6. Apparatus according to claim 1 wherein both standing waves have said axes of propagation directed obliquely to the column longitudinal axis, said axes of propagation lying essentially in a common plane whereby said intersections lie normal to the longitudinal axis.

7. Apparatus according to claim 6 wherein the generating means are arranged to produce standing waves that extend across the column at opposite and equiangular inclinations to the column axis.

8. Apparatus according to claim 7 having means for producing two intersecting standing waves by reflection from a single source.

9. A method of controlling movement of particulate material in a liquid column utilizing a standing wave system produced by ultrasonic energy generating means, said method comprising the steps of:
 establishing at least two ultrasonic standing waves, each standing wave having a series of nodes with at least some of the nodes of the respective standing waves intersecting in the column, the column having a longitudinal axis and said standing waves having axes of propagation extending transversely across the column at different orientations relative to the column longitudinal axis, at least one of the standing waves having its axis of propagation extending obliquely to the column longitudinal axis, whereby said nodes of the standing waves have intersections that are angled relative to said longitudinal axis; and
 performing a relative movement in the direction of said longitudinal axis between said intersections at the nodes and the particle-containing liquid in the column, and retaining at least some of the particles in the regions of said intersections while said relative motion is performed.

10. A method according to claim 9 further comprising the step of refracting at least one of the standing waves to an axial direction lying more closely to a perpendicular to the column axis by directing said at least one standing wave into the column through a coupling medium having a sonic velocity substantially greater than the sonic velocity in the column.

11. A method according to claim 9 wherein the step of establishing said at least two standing waves includes creating two standing waves having axes of propagation that lie in different and mutually angled planes that extend axially of the column.

12. A method according to claim 9 wherein the step of establishing the standing wave includes creating standing waves that extend across the column at opposite and equiangular inclinations relative to the column axis.

13. A method according to claim 12 wherein the establishing step includes producing two intersecting standing waves by reflection from a single source.

14. A method according to claim 9 further comprising the step of producing each standing wave wholly or mainly by reflection from a respective single source.

15. A method according to claim 9 wherein the establishing step includes creating two standing waves, one of said waves having its axis of propagation perpendicular to the column and is operated in a resonant mode in the column, and the other of said two standing waves having its axis of propagation oblique to the axis of the column and is operated in a non-resonant mode in the column, the nodes of the second standing wave being given a movement to carry particles with them along the column.

16. Apparatus for controlling movement of particulate material in a liquid column, comprising:
 generating means for producing at least two ultrasonic standing waves, each standing wave having a series of nodes and the respective series of nodes intersecting within said column, said standing waves having axes extending transversely across the column and the column having a longitudinal axis relative to which the standing waves have different orientations, whereby the nodes of the standing wave intersect within the columns; and
 means for relative movement along the column between the intersections of the nodes of the standing waves and the particle-containing liquid in the column;
 wherein coupling means are disposed between the generating means for at least one of the standing waves and the column, and said coupling means having emitting faces lying oblique to the axis of propagation of said standing wave therethrough, said coupling means being of a medium in which the sonic velocity is substantially higher than in the liquid of the column.

17. Apparatus for controlling movement of particulate material in a liquid column, comprising:
 generating means for producing at least two ultrasonic standing waves, each standing wave having a series of nodes and the respective series of nodes intersecting within said column, said standing waves having axes extending transversely across the column and the column having a longitudinal axis relative to which the standing waves have different orientations, whereby the nodes of the standing wave intersect with the column; and
 means for relative movement along the column between the intersections of the nodes of the standing waves and the particle-containing liquid in the column;
 wherein coupling means are disposed between the generating means for at least one of the standing waves and the column, and said coupling means have emitting faces perpendicular to the axis of propagation of said standing wave but oblique to the longitudinal axis of the column.

18. A method of controlling movement of particulate material in a liquid column by means of a standing wave system produced by ultrasonic energy generating means, said method comprising the steps of:
 establishing at least two ultrasonic standing waves each having an axis extending transversely across the column, the column having a longitudinal axis relative to which the axes of said standing waves are at different orientations, the standing waves having nodes that thereby intersect within the column;
 performing a relative movement along the column between the intersections of the nodes of the standing waves in the column and the particle-containing liquid therein;

retaining at least some of the particles in said fluid in the regions of said intersections while said relative movement is performed; and refracting at least one of said standing waves to an axial direction lying more closely to a perpendicular to the column axis by directing said at least one standing wave into the column through a coupling medium having a sonic velocity substantially greater than the sonic velocity in the column.

19. A method of controlling movement of particulate material in a liquid column by means of a standing wave system produced by ultrasonic energy generating means, said method comprising the steps of:

establishing at least two ultrasonic standing waves each having an axis extending transversely across the column, the column having a longitudinal axis relative to which the axes of said standing waves are at different orientations, the standing waves having nodes that thereby intersect within the column;

performing a relative movement along the column between the intersections of the nodes of the standing waves in the column and the particle-containing liquid therein; and retaining at least some of the particles in said fluid in the regions of said intersections while said relative movement is performed;

wherein the establishing step includes creating two standing waves, one of said waves having its axis of propagation perpendicular to the column and is operated in a resonant mode in the column, and the other of said two standing waves having its axis of propagation oblique to the axis of the column and is operated in a non-resonant mode in the column, the nodes of the second standing wave being given a movement of carry particles with them along the column.

* * * * *